US012318798B2

(12) United States Patent
Kawasaki et al.

(10) Patent No.: US 12,318,798 B2
(45) Date of Patent: Jun. 3, 2025

(54) MIST SUPPLY DEVICE

(71) Applicant: AIREX CO., LTD., Nagoya (JP)

(72) Inventors: Koji Kawasaki, Nagoya (JP); Daisuke Kakuda, Nagoya (JP); Jun Masudome, NNagoya (JP); Haruka Futamura, Nagoya (JP); Yukihiro Yazaki, Nagoya (JP); Tsukasa Kitano, Nagoya (JP); Zhiqiang Guo, Nagoya (JP); Ayumi Ogawa, Nagoya (JP)

(73) Assignee: AIREX CO., LTD. (JP)

( * ) Notice: Subject to any disclaimer, the term of this patent is extended or adjusted under 35 U.S.C. 154(b) by 868 days.

(21) Appl. No.: 17/601,528

(22) PCT Filed: Mar. 18, 2020

(86) PCT No.: PCT/JP2020/011878
§ 371 (c)(1),
(2) Date: Oct. 5, 2021

(87) PCT Pub. No.: WO2020/209020
PCT Pub. Date: Oct. 15, 2020

(65) Prior Publication Data
US 2022/0176401 A1    Jun. 9, 2022

(30) Foreign Application Priority Data
Apr. 9, 2019   (JP) .................................. 2019-073855

(51) Int. Cl.
*A61L 2/18*    (2006.01)
*B05B 17/06*   (2006.01)

(52) U.S. Cl.
CPC ............... *B05B 17/06* (2013.01); *A61L 2/18* (2013.01)

(58) Field of Classification Search
CPC ... B05B 7/0012; B05B 17/06; B05B 17/0615; B05B 17/0646; A61L 2/22; A61L 2/18; A61L 2/025; A61L 2202/25
See application file for complete search history.

(56) References Cited

U.S. PATENT DOCUMENTS 4,257,989 A * 3/1981 Nishikawa .......... B05B 17/0615
                                            210/287
4,983,189 A * 1/1991 Peterson ................ B01D 43/00
                                            366/127

(Continued)

FOREIGN PATENT DOCUMENTS

JP        H04118066 A     4/1992
JP        2006204968 A    8/2006

(Continued)

OTHER PUBLICATIONS

PCT International Search Report, PCT/JP2020/011878, May 26, 2020, 6 pages.

*Primary Examiner* — Joseph A Greenlund
(74) *Attorney, Agent, or Firm* — Quarles & Brady LLP; Yakov S. Sidorin (57) ABSTRACT

A mist supply device configured to decontaminate a target with a proper amount of decontamination agent supplied to the target by converting such agent into a fine mist, and reducing the duration of operations such as aeration to increase decontamination efficiency. The device includes a mist generation means, a mist microparticulating means, and a supply port. The mist generation means converts the decontamination agent into a primary mist and supplies it to the mist microparticulating means, which includes at least one vibration board that is subjected to ultrasonic vibration to generate sound flows from board surfaces by an ultrasound in the vertical direction. The supplied primary mist is subjected to ultrasonic vibration by the sound flows to (Continued)

reduce the primary mist into a secondary mist of smaller size. The generated secondary mist is supplied to the inside of the room through the supply port.

7 Claims, 4 Drawing Sheets

(56) References Cited

U.S. PATENT DOCUMENTS

| | | | | |
|---|---|---|---|---|
| 5,225,089 | A * | 7/1993 | Benes | B01D 43/00 366/127 |
| 8,114,203 | B2 * | 2/2012 | Kim | B01D 45/04 55/428 |
| 9,533,064 | B1 * | 1/2017 | Adiga | A61L 9/14 |
| 9,744,256 | B2 * | 8/2017 | Gschwind | A61L 9/14 |
| 10,688,536 | B2 * | 6/2020 | Ponomarev | B08B 7/028 |
| 11,984,314 | B2 * | 5/2024 | Huang | G03F 1/82 |
| 12,115,564 | B2 * | 10/2024 | Kirkby | B08B 7/028 |
| 2008/0223953 | A1 * | 9/2008 | Tomono | A61M 11/005 128/200.16 |
| 2008/0290189 | A1 * | 11/2008 | Levi | A01M 1/2055 239/102.2 |
| 2010/0143189 | A1 * | 6/2010 | Martin | A61L 2/208 422/292 |
| 2012/0251296 | A1 * | 10/2012 | Jorgensen | B05B 17/0607 415/116 |
| 2013/0079733 | A1 * | 3/2013 | Burt | B08B 3/12 239/102.1 |
| 2014/0008307 | A1 * | 1/2014 | Guldiken | B01L 3/502761 422/502 |
| 2014/0332606 | A1 * | 11/2014 | Asakawa | B05B 7/0012 239/428 |
| 2014/0336062 | A1 * | 11/2014 | Graves | G01N 15/1404 506/7 |
| 2015/0191766 | A1 * | 7/2015 | Kobayashi | A61L 2/186 435/309.1 |
| 2015/0239020 | A1 * | 8/2015 | Ponomarev | B08B 7/028 134/1 |
| 2016/0067368 | A1 * | 3/2016 | Gschwind | A61L 9/14 239/4 |
| 2018/0099259 | A1 * | 4/2018 | Kawasaki | B01D 49/006 |
| 2022/0152667 | A1 * | 5/2022 | Kawasaki | B08B 7/028 |
| 2022/0176401 | A1 * | 6/2022 | Kawasaki | A61L 2/025 |
| 2022/0193290 | A1 * | 6/2022 | Kawasaki | A61L 2/26 |
| 2022/0248924 | A1 * | 8/2022 | Karren | C02F 1/4618 |
| 2022/0370666 | A1 * | 11/2022 | Kawasaki | A61L 9/14 |
| 2022/0378964 | A1 * | 12/2022 | Kawasaki | F24F 8/24 |
| 2023/0042650 | A1 * | 2/2023 | Ross | A61L 2/24 |
| 2023/0347002 | A1 * | 11/2023 | Kitano | A61L 2/26 |

FOREIGN PATENT DOCUMENTS

| | | |
|---|---|---|
| JP | 2006296617 A | 11/2006 |
| JP | 2007075243 A | 3/2007 |
| WO | 2006095816 A1 | 9/2006 |

* cited by examiner

MIST SUPPLY DEVICE

CROSS-REFERENCE TO RELATED APPLICATIONS

This application represents the US national stage entry from the International Application No. PCT/JP2020/011828, filed on Mar. 18, 2020, that claims priority from the Japanese Patent Application No. JP 2019-073855 filed on Apr. 9, 2019. The disclosure of each of the above-identified patent documents is incorporated by reference herein.

TECHNICAL FIELD

The present invention relates to a mist supply device for supplying a decontamination agent by converting the same into a mist and, more particularly, to a mist supply device for supplying a secondary mist obtained by further refining a primary mist.

BACKGROUND ART

In manufacturing settings for pharmaceutical or food products or in the clinical environment such as operating rooms, the indoor working area must inevitably be kept sterile. Particularly in cases where clean rooms as a working chamber for manufacturing pharmaceutical products are decontaminated, advanced decontamination validation needs to be accomplished in accordance with Good Manufacturing Practice (GMP).

In recent years, hydrogen peroxide has widely been used (in the form of a gas or mist) to decontaminate a working chamber such as a sterile room (hereinafter referred to as a "room to be decontaminated"). Advantageously, hydrogen peroxide has a strong sterilization effect, and is inexpensively available and effectively utilized as an environmentally-friendly decontamination gas that is ultimately resolved into oxygen and water. Thus, the following patent document 1 and many other documents propose efficient supply of a hydrogen peroxide solution by gasification to the inside of a room to be decontaminated.

Meanwhile, the following patent document 1 describes that the decontamination effect by hydrogen peroxide is provided by a condensed film of a hydrogen peroxide solution that condenses on the surface of an object to be decontaminated. Specifically, a hydrogen peroxide gas supplied by gasification is condensed on the surface of the object to be decontaminated such as a wall surface of a room to be decontaminated for decontamination. Consequently, in order to accomplish a decontamination effect of a room to be decontaminated and more efficient decontamination works, hydrogen peroxide gas may be supplied in large quantities to swiftly generate the resulting condensed film of a hydrogen peroxide solution or a hydrogen peroxide solution may be provided in the form of liquid (e.g., in the form of liquid droplet).

CITATION LIST

Patent Literature

Patent Document 1: JP-A-2006-320392 A
Patent Document 2: JP-A-61-004543

SUMMARY OF THE INVENTION

Technical Problem

In fact, the supply of an excessive amount of hydrogen peroxide to a room to be decontaminated or a direct supply of liquid droplets of a hydrogen peroxide solution causes extreme or uneven condensation, and the resulting condensed film from a high concentration of hydrogen peroxide solution disadvantageously corrodes production equipment, precise measuring equipment and wall surfaces and other portions of a room to be contaminated. After a decontamination work using hydrogen peroxide, aeration is performed with clean air to remove the residual hydrogen peroxide and condensed film inside the room to be decontaminated. However, the supply of such an excessive amount of hydrogen peroxide is problematic due to longer duration required in the aeration operation for removing a high concentration of condensed film of a hydrogen peroxide solution generated on wall surfaces and other portions of the room to be decontaminated.

Thus, the present invention was made in view of the situation to solve the problems, and has an object to provide a mist supply device capable of accomplishing a decontamination effect with a proper amount of decontamination agent supplied to a room to be decontaminated by converting a decontamination agent into a fine mist, and reducing the duration of operations such as aeration to achieve more efficient decontamination works.

Solution to the Problem

To solve the aforementioned problem, inventors of the present invention have carried out an extended investigation to find that a decontamination agent is converted into a mist and then the mist is subjected to ultrasonic vibration to obtain a further refined mist. Based on that technique, the present invention was accomplished.

Specifically, a mist supply device according to the present invention is, according to description in claim 1, a supply device (10, 110, 210) for converting a decontamination agent into a mist and supplying the same to the inside of a room to be decontaminated, including a mist generation means (30, 130, 230), a mist microparticulating means (40, 140, 240), and a supply port (50, 150, 250), characterized in that the mist generation means converts the decontamination agent into a primary mist (32, 132, 232) and supplies the same to the mist microparticulating means, the mist microparticulating (that is, mist size reducing) means includes one or more vibration boards (41, 42, 141, 142), and the vibration board(s) is/are subjected to ultrasonic vibration to generate sound flows from board surfaces (41a, 42a, 141a, 142a) by an ultrasound in the vertical direction, the primary mist supplied from the mist generation means is subjected to ultrasonic vibration by the sound flows to further refine the primary mist into a secondary mist (33, 133, 233), and the generated secondary mist is supplied to the inside of the room to be decontaminated through the supply port.

Furthermore, the present invention is, according to description in claim 2, the mist supply device according to claim 1, characterized in that the mist generation means is a spray nozzle such as a single-fluid nozzle or a two-fluid nozzle (31), or an ultrasonic mist generator such as an ultrasonic humidifier or a nebulizer (131, 231).

Moreover, the present invention is, according to description in claim 3, the mist supply device according to claim 1 or 2, characterized in that the mist microparticulating means includes one or more pairs of vibration boards, the pair(s) of vibration boards are arranged with board surfaces thereof being opposite each other from an outer peripheral side of the primary mist supplied from the mist generation means, whereby ultrasonic vibration by the sound flows is controlled to concentrate on the primary mist.

Furthermore, the present invention is, according to description in claim 4, the mist supply device according to claim 1 or 2, characterized in that the mist microparticulating means includes a combination of one or more pairs of vibration boards (241) and reflection boards (242), the combination of the pair(s) of vibration boards and reflection boards is arranged with the respective vibration surfaces (241*a*) and reflection surfaces (242*a*) being opposite from an outer peripheral side of the primary mist supplied from the mist generation means, whereby ultrasonic vibration by sound flows generated from the vibration boards and sound flows reflecting off the reflection boards is controlled to concentrate on the primary mist.

Moreover, the present invention is, according to description in claim 5, the mist supply device according to claim 4, characterized in that the supply port includes board surfaces of all or part of the vibration boards as a supply means of the secondary mist, and the secondary mist is pressed by acoustic radiation pressure by sound flows generated from the board surfaces to supply the secondary mist to the inside of the room to be decontaminated.

Furthermore, the present invention is, according to description in claim 6, the mist supply device according to any one of claims 1 to 5, characterized in that the vibration table (41) includes a base (61) and a plurality of transmitters (63), the plurality of transmitters is arranged on a plane or planar surface (62) of the base so as to be uniform in transmission directions, and the transmitters are operated in the same phase, whereby a sound flow is generated by a significantly directional ultrasound from the board surface of the vibration board in the vertical direction by mutually amplifying the ultrasounds of the plurality of transmitters in the front direction and mutually canceling out the ultrasounds of the plurality of transmitters in the lateral direction.

Advantageous Effects of the Invention

According to the above configuration, the mist supply device of the present invention includes a mist generation means, a mist microparticulating means, and a supply port. The mist generation means converts a decontamination agent into a primary mist and supplies the same to the mist microparticulating means. The mist microparticulating (size-reducing) means includes one or more vibration boards, and the vibration board(s) is/are subjected to ultrasonic vibration to generate sound flows from board surfaces by an ultrasound in the vertical direction. The primary mist supplied from the mist generation means is subjected to ultrasonic vibration by the sound flows to further refine the primary mist into a secondary mist the dimensions of the mist particles of which are now substantially reduced. The generated secondary mist is supplied to the inside of the room to be decontaminated through the supply port.

According to the above configuration, the present invention can provide a mist supply device capable of accomplishing a decontamination effect with a proper amount of decontamination agent supplied to a room to be decontaminated by converting a decontamination agent into a fine mist, and reducing the duration of operations such as aeration to achieve more efficient decontamination works.

According to the above configuration, the mist generation means may be a spray nozzle such as a single-fluid nozzle or a two-fluid nozzle, or an ultrasonic mist generator such as an ultrasonic humidifier or a nebulizer. Thus, the above operational advantage can more specifically be provided.

According to the above configuration, the mist microparticulating means may include one or more pairs of vibration boards. The pair(s) of vibration boards are arranged with board surfaces thereof being opposite each other from an outer peripheral side of the primary mist supplied from the mist generation means. Accordingly, ultrasonic vibration by the sound flows is controlled to concentrate on the primary mist. Thus, the above operational advantage can more specifically be provided.

According to the above configuration, the mist microparticulating means may include a combination of one or more pairs of vibration boards and reflection boards. The combination of the pair(s) of vibration boards and reflection boards is arranged with the respective vibration surfaces and reflection surfaces being opposite from an outer peripheral side of the primary mist supplied from the mist generation means. Accordingly, ultrasonic vibration by sound flows generated from the vibration boards and sound flows reflecting off the reflection boards concentrates on the primary mist. Thus, the above operational advantage can more specifically be provided.

According to the above configuration, the supply port may include board surfaces of all or part of the vibration boards as a supply means of the secondary mist. The secondary mist is pressed by acoustic radiation pressure by sound flows generated from the board surfaces. Accordingly, the secondary mist is supplied to the inside of the room to be decontaminated. Thus, the above operational advantage can more specifically be provided. Thus, the above operational advantage can more specifically be provided.

According to the above configuration, the vibration board may include a base and a plurality of transmitters, and the plurality of transmitters may be arranged on a plane or planar surface of the base so as to be uniform in transmission directions, and the transmitters may be operated in the same phase. Consequently, the ultrasounds of the plurality of transmitters in the front direction are mutually amplified, and the ultrasounds of the plurality of transmitters in the lateral direction are mutually canceled out. Accordingly, a sound flow can be generated by a significantly directional ultrasound from the board surface of the vibration board in the vertical direction. Thus, the above operational advantage can more specifically be provided.

DETAILED DESCRIPTION

The mist supply device according to the present invention refers to a supply device for supplying a decontamination agent to the inside of rooms to be decontaminated to decontaminate the inside of such rooms to be decontaminated as a clean room or isolator, the inside of a pass box linked to such a room to be decontaminated, or an apparatus or article to be decontaminated disposed inside these rooms to be decontaminated. The mist supply device according to the present invention also refers to a supply device for supplying a decontamination agent by converting the same into a fine mist, as opposed to conventional supply devices for supplying a decontamination agent by gasification.

In addition, the mist supply device according to the present invention is used not only in supplying a decontamination agent by converting the same into a fine mist, but also in supplying other liquids such as water by converting the same into a fine mist. For example, the mist supply device according to the present invention may be used to supply a fine water mist (also called as "fog") indoor when controlling the humidity of the inside of an isolator prior to decontamination or controlling the humidity appropriate for decontamination.

In the present invention, "mist" is broadly interpreted as the state of a liquid droplet of a decontamination agent refined and floating in the air, the state of a gas and a liquid agent of a decontamination agent in mixture, the state of the decontamination agent to repeat the change in phase between condensation and evaporation of a gas and a droplet, and the like. In terms of particle size as well, the mist is also broadly interpreted to include mists, fogs, and liquid droplets, which can be subclassified.

Accordingly, the primary mist according to the present invention is categorized into a "mist" (the size may be defined as 10 μm or less) or a "fog" (the size may be defined as 5 μm or less), and a mist having a larger particle size. The secondary mist in the present invention refers to a refined primary mist by ultrasonic vibration. In particular, the secondary mist in the present invention is believed to provide high-level decontamination effects even for a short period of time in that primary mists such as a mist, a fog and a liquid droplet (liquid droplets sized 3 to 10 μm, or a larger particle size) are equalized into ultrafine particles 3 μm or less by ultrasonic vibration (later described).

The mist supply device according to the present invention will be described in detail with reference to each embodiment. The present invention is not restricted to each of the following embodiments. In the mist supply device according to each of the following embodiments, a decontamination agent used is a hydrogen peroxide solution. The decontamination agent supplied by the mist supply device according to the present invention is not restricted to a hydrogen peroxide solution, and it may be any type of decontamination agent such as a peracetic aqueous solution so long as it is liquid.

First Embodiment

This first embodiment relates to a mist supply device for supplying a hydrogen peroxide solution mist as a decontamination agent to the inside of an isolator or the like by communicating with a bottom wall surface of the isolator or the like. FIG. 1 is a cross-sectional view showing the inside of the mist supply device according to the first embodiment from the side. In FIG. 1, a mist supply device 10 includes a housing 20 made of stainless metal plate, a mist generator 30 for generating a primary mist, a mist refining device 40 for further refining the generated primary mist into a secondary mist, and a supply port 50 for discharging the generated secondary mist.

The mist generator 30 converts a decontamination agent into a primary mist and supplies the same to the mist refining device 40. In this first embodiment, the mist generator 30 used is a two-fluid spray nozzle 31, which is disposed on a bottom wall surface of the housing 20. In this first embodiment, the decontamination agent used is a hydrogen peroxide solution (35 W/V %).

The two-fluid spray nozzle 31 converts a hydrogen peroxide solution into a hydrogen peroxide solution mist 32 as a primary mist by compressed air from a compressor (not shown) to supply the same to the inside of the mist refining device 40. In the first embodiment, the mist generator is not restricted to a two-fluid spray nozzle, and a mist generation means and output are not particularly restricted.

The mist refining device 40 includes 2 vibration boards 41, 42. The 2 vibration boards 41, 42 are disposed against the inside of 2 opposite side wall surfaces 22, 23 of the housing 20 such that vibration surfaces 41*a*, 42*a* face in the horizontal direction toward an upper portion of the mist discharge port 31*a* of the two-fluid spray nozzle 31. The mist refining device 40 refines the hydrogen peroxide solution mist 32 generated as the primary mist by the two-fluid spray nozzle 31 into a fine mist 33 as a secondary mist. The details of refinement will be described later.

A supply port 50 is open on a top wall surface 24 of the housing 20, and supplies a fine mist 33 refined as a secondary mist by the mist refining device 40 to the inside of an isolator (not shown) communicating with an upper portion of the housing 20.

Herein, the vibration table 41 (also applied to the vibration table 42) will be described. FIG. 2 is a schematic perspective view showing a plurality of ultrasonic speakers arranged in a speaker base in vibration boards included in a mist refining device 40 according to this first embodiment. In FIG. 2, the vibration board 41 includes a base and a plurality of transmitters. In this first embodiment, the base used is a speaker base 61, and the transmitter used is an ultrasonic speaker 63. In this first embodiment, 25 ultrasonic speakers 63 are arranged on a plane or planar surface 62 of the speaker base 61 so as to be uniform in transmission direction of a vibration surface 64 (leftward as seen from the front shown). The number of ultrasonic speakers is not particularly restricted.

In this first embodiment, the ultrasonic speaker 63 used is an ultra directional ultrasonic speaker. Specifically, ultrasonic speakers (DC12V, 50 mA) of frequency modulation system transmitting a frequency near 40 KHz are used. The type, size, structure and output of ultrasonic speakers are not particularly restricted. In the first embodiment, the vibration board included in the mist refining device 40 is not restricted to an ultrasonic speaker, and the ultrasonic generation means and output are not particularly restricted.

In this first embodiment, a plurality of (25) ultrasonic speakers 63 are arranged so as to be uniform in transmission direction of the vibration surface 64, and the transmitters are operated in the same phase to mutually amplify ultrasounds from the plurality of ultrasonic speakers 63 in the front direction and mutually cancel out ultrasounds from the plurality of ultrasonic speakers 63 in the lateral direction. Consequently, the ultrasonic speakers 63 arranged on the speaker base 61 are subjected to ultrasonic vibration to generate a significantly directional sound flow traveling in the air from each of the vibration surfaces 64 in the vertical direction. The frequency and output of the ultrasonic speakers 63 are controlled by an ultrasonic controller (not shown) to achieve efficient refinement effects.

Figure 1:
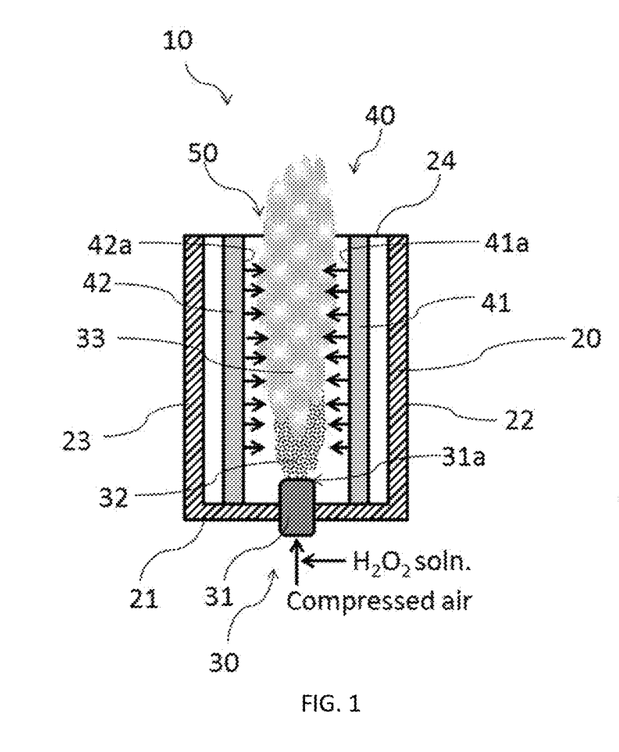
FIG. 1 is a cross-sectional view showing the inside of a mist supply device according to a first embodiment from the side.

Subsequently, the action of the hydrogen peroxide solution mist 32 and the fine mist 33 inside the mist supply device 10 according to the above configuration will be described with reference to FIG. 1.

Ultrasonic vibration of the ultrasonic speaker 63 of each of the vibration boards 41, 42 in this state generates significantly directional sound flows traveling in the vertical direction from the 2 vibration surfaces 41a, 42a, respectively (indicated by arrows from board surfaces). The sound flows generated from the vibration surfaces 41a, 42a of the vibration boards 41, 42 act on the hydrogen peroxide solution mist 32 discharged from the two-fluid spray nozzle 31. The hydrogen peroxide solution mist 32 travels upward in the figure shown (in the direction of the supply port 50) by a releasing pressure from the two-fluid spray nozzle 31. At this time, the hydrogen peroxide solution mist 32 is highly refined into the fine mist 33 by ultrasonic vibration by the sound flows generated from the vibration surfaces 41a, 42a, and travels upward in the figure shown to be supplied to the inside of an isolator (not shown) communicating with an upper portion from the supply port 50.

In fact, since the fine mist 33 is refined by ultrasonic vibration to have smaller particle sizes and larger surface areas, it is believed that the evaporation efficiency of mists is high, resulting in repeated evaporation and condensation. The fine mist 33 is a highly-refined mist to form a uniform and thin condensed film on an internal wall surface of the isolator and external surfaces of onboard equipment disposed therein. Therefore, no excessive condensation occurs on internal wall surfaces of the isolator or external surfaces of internal equipment.

Accordingly, the fine mist 33 of hydrogen peroxide is subjected to ultrasonic vibration to be supplied to the inside of the isolator, thereby allowing the resulting repeated evaporation, condensation and refinement to provide decontamination effects. Accordingly, inside the isolator, ultrafine particles of hydrogen peroxide 3 μm or less and a hydrogen peroxide gas are subjected to phase change for coexistence to provide high-level decontamination environment.

Also, by repeated re-evaporation and condensation of the uniformly and thinly formed condensed film on the internal wall surfaces of the isolator and the external surfaces of internal equipment, the concentration of a decontamination agent in a fine mist 33 can be increased and efficient decontamination can be performed with a small amount of decontamination agent. Such an efficient decontamination with a small amount of decontamination agent can improve the efficiency of aeration for a condensed film of the fine mist 33 that is residual inside an isolator and reduce the duration of decontamination operations.

Second Embodiment

This second embodiment relates to a mist supply device for supplying a hydrogen peroxide solution mist as a decontamination agent to the inside of an isolator or the like by communicating with a bottom wall surface of the isolator or the like as well as the above first embodiment. In this second embodiment, the structure of a mist generator is different from that in the first embodiment. FIG. 3 is a cross-sectional view showing the inside of a mist supply device according to this second embodiment from the side. In FIG. 3, a mist supply device 110 includes a housing 120 made of stainless metal plate, a mist generator 130 for generating a primary mist, a mist refining device 140 for further refining the generated primary mist into a secondary mist, and a supply port 150 for discharging the generated secondary mist.

The mist generator 130 converts a decontamination agent into a primary mist and supplies the same to the mist refining device 140. In this second embodiment, the mist generator 130 used is a nebulizer 131, which is disposed on a bottom wall surface 121 of a housing 120. In this second embodiment, the decontamination agent used is a hydrogen peroxide solution (35 W/V %) as well as in the above first embodiment.

The nebulizer 131 includes a main container 131*b* for accommodating a hydrogen peroxide solution supplied from the outside and including a mist discharge port 131*a*, and an ultrasonic vibrator 131*c* disposed therein. Ultrasonic vibration of the ultrasonic vibrator 131*c* immersed in a hydrogen peroxide solution in this state converts the hydrogen peroxide solution into a primary mist as a hydrogen peroxide solution mist 132 to supply the same to the mist refining device 140. In the second embodiment, the mist generator is not restricted to a nebulizer, and a mist generation means and output are not particularly restricted.

The mist refining device 140 is in the same structure as the above first embodiment, and includes 2 vibration boards 141, 142. The 2 vibration boards 141, 142 are disposed against the inside of 2 opposite side wall surfaces 122, 123 of the housing 120 such that vibration surfaces 141*a*, 142*a* face in the horizontal direction toward an upper portion of the mist discharge port 131*a* of the main container 131*b* of the nebulizer 131. The mist refining device 140 refines a hydrogen peroxide solution mist 132 generated as the primary mist by the nebulizer 131 into a fine mist 133 as a secondary mist. The details of refinement will be described later. The structure of 2 vibration boards 141, 142 is the same as in the above first embodiment (see FIG. 2).

A supply port 150 is open on a top wall surface 124 of the housing 120, and supplies the fine mist 133 refined as a secondary mist by the mist refining device 140 to the inside of an isolator (not shown) communicating with an upper portion of the housing 120.

Subsequently, the action of the hydrogen peroxide solution mist 132 and the fine mist 133 inside the mist supply device 110 according to the above configuration will be described with reference to FIG. 3.

Ultrasonic vibration of the ultrasonic speaker 63 of each of the vibration boards 141, 142 in this state (see FIG. 2) generates significantly directional sound flows traveling in the vertical direction from the 2 vibration surfaces 141*a*, 142*a*, respectively (indicated by arrows from board surfaces). The sound flows generated from the vibration surfaces 141*a*, 142*a* of the vibration boards 141, 142 act on the hydrogen peroxide solution mist 132 discharged from the nebulizer 131. The hydrogen peroxide solution mist 132 travels upward in the figure shown (in the direction of the supply port 150) by a releasing pressure from the nebulizer 131. At this time, the hydrogen peroxide solution mist 132 is highly refined into the fine mist 133 by ultrasonic vibration by the sound flows generated from the vibration surfaces 141*a*, 142*a*, and travels upward in the figure shown to be supplied to the inside of an isolator (not shown) communicating with an upper portion from the supply port 150.

In fact, since the fine mist 133 is refined by ultrasonic vibration to have smaller particle sizes and larger surface areas, it is believed that the evaporation efficiency of mists is high, resulting in repeated evaporation and condensation. The fine mist 133 is a highly-refined mist to form a uniform and thin condensed film on an internal wall surface of the isolator and external surfaces of onboard equipment disposed therein. Therefore, no excessive condensation occurs on internal wall surfaces of the isolator or external surfaces of internal equipment.

Accordingly, the fine mist 133 of hydrogen peroxide is subjected to ultrasonic vibration to be supplied to the inside of the isolator, thereby allowing the resulting repeated evaporation, condensation and refinement to provide decontamination effects.

Accordingly, inside the isolator, ultrafine particles of hydrogen peroxide 3 μm or less and a hydrogen peroxide gas are subjected to phase change for coexistence to provide high-level decontamination environment.

Also, by repeated re-evaporation and condensation of the uniformly and thinly formed condensed film on the internal wall surfaces of the isolator and the external surfaces of internal equipment, the concentration of a decontamination agent in a fine mist 133 can be increased and efficient decontamination can be performed with a small amount of decontamination agent. Such an efficient decontamination with a small amount of decontamination agent can improve the efficiency of aeration for a condensed film of the fine mist 133 that is residual inside an isolator and reduce the duration of decontamination operations.

Third Embodiment

Figure 4A:
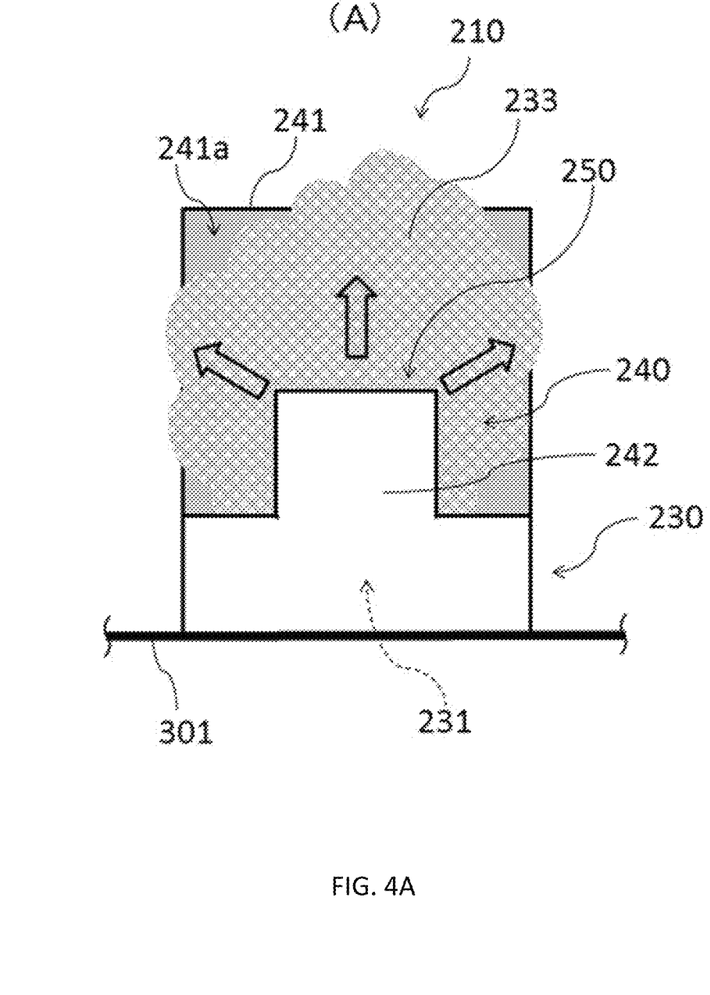
FIG. 4A is a front view of a mist supply device according to a third embodiment and FIG. 4B is a cross-sectional view showing the inside thereof from the side.
Figure 4B:
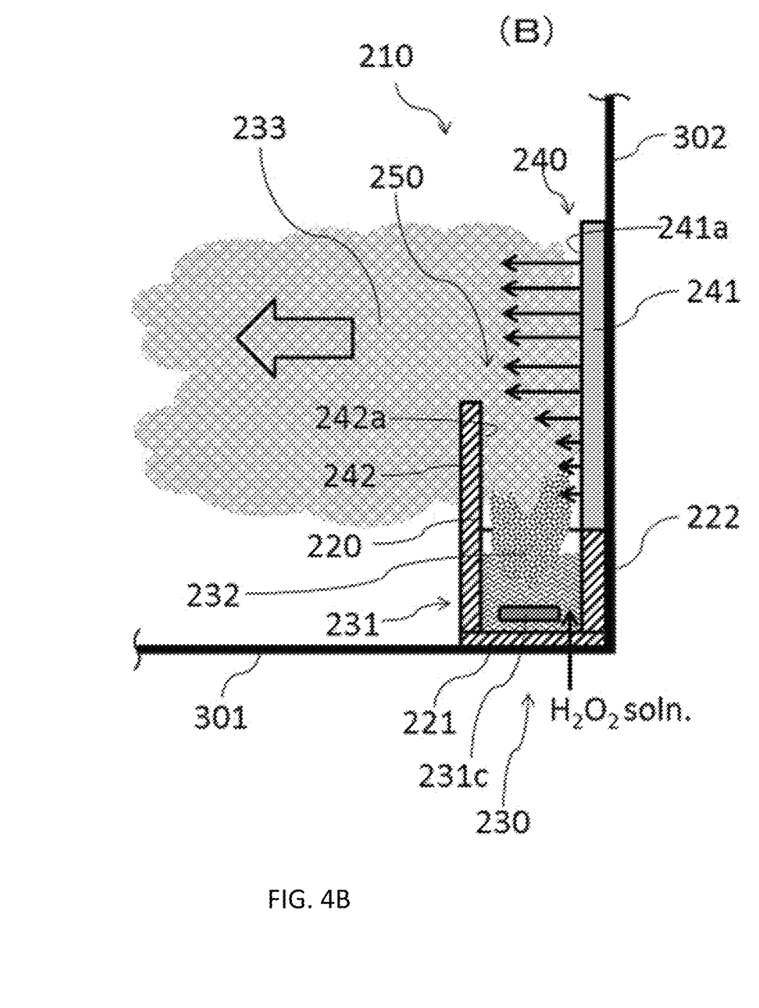

This third embodiment relates to a mist supply device disposed inside an isolator for supplying a hydrogen peroxide solution mist as a decontamination agent to the inside of the isolator as opposed to the above first and second embodiments. FIG. 4A is a front view of a mist supply device according to the third embodiment and FIG. 4(B) is a cross-sectional view showing the inside thereof from the side. In FIGS. 4A, 4B, a mist supply device 210 includes a housing 220 made of stainless metal plate, a mist generator 230 for generating a primary mist, a mist refining device 240 for further refining the generated primary mist into a secondary mist, and a supply port 250 for discharging the generated secondary mist.

In this third embodiment, the mist supply device 210 is disposed such that a bottom wall surface 221 thereof contacts with internal wall surfaces of a bottom wall surface 301 of an isolator body (not shown) and a side wall surface 222 thereof contacts with internal wall surfaces of a side wall surface 302 of the isolator body to allow the supply port 250 to be open inside the isolator body.

The mist generator 230 converts a decontamination agent into a primary mist and supplies the same to the mist refining device 240. In this third embodiment, the mist generator 230 used is a nebulizer 231. In this third embodiment, the decontamination agent used is a hydrogen peroxide solution (35 W/V %) as well as in the above first embodiment.

The nebulizer 231 constitutes a base of the housing 220, including therein an ultrasonic vibrator 231c. Ultrasonic vibration of the ultrasonic vibrator 231c immersed in a hydrogen peroxide solution in this state converts the hydrogen peroxide solution into a primary mist as a hydrogen peroxide solution mist 232 to supply the same to the mist refining device 240. In the third embodiment, the mist generator is not restricted to a nebulizer, and a mist generation means and output are not particularly restricted.

Figure 2:
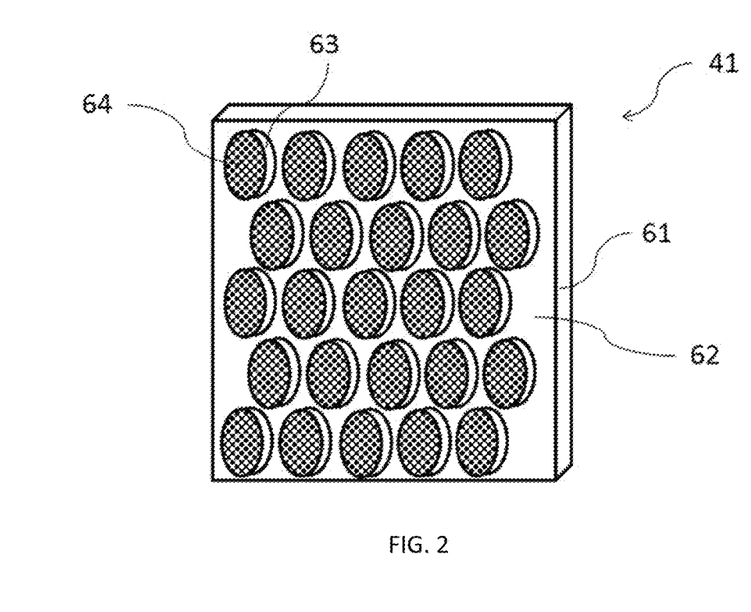
FIG. 2 is a schematic perspective view showing a plurality of ultrasonic speakers arranged in a speaker base in vibration boards included in a mist refining device according to the first embodiment.
Figure 3:
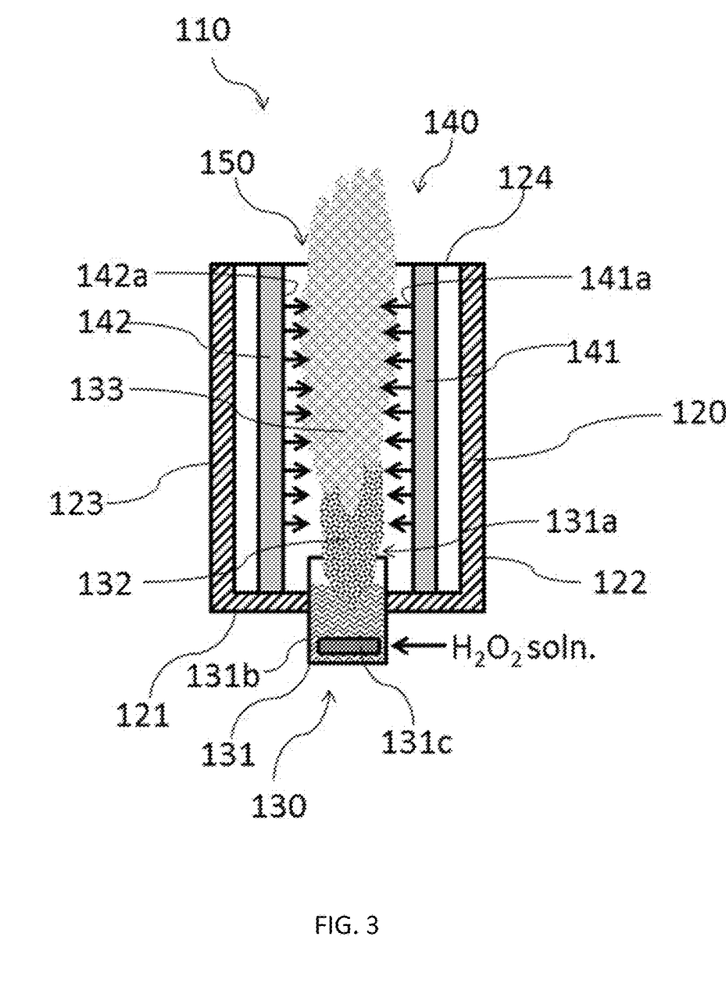
FIG. 3 is a cross-sectional view showing the inside of a mist supply device according to a second embodiment from the side.

The mist refining device 240 includes a pair of a vibration board 241 and a reflection board 242. The pair of a vibration board 241 and a reflection board 242 are disposed upward from the nebulizer 231 such that they face a central portion in the vertical direction of the housing 220 by allowing a vibration surface 241a and a reflection surface 242a to be opposite in the horizontal direction. The vibration board 241 is disposed with larger dimensions in height and width than the reflection board 242, and a portion of the vibration surface 241a that is not opposite the reflection board 242 is open inside the isolator (see FIG. 4A). The mist refining device 240 thus configured refines the hydrogen peroxide solution mist 232 generated as the primary mist by the nebulizer 231 into a fine mist 233 as a secondary mist. The details of refinement will be described later. The structure of the vibration board 241 is the same as in the above first embodiment (see FIG. 2).

The supply port 250 is open at an upper portion and right/left side portions of the reflection board 242 upwardly from the housing 220, and supplies a fine mist 233 refined as a secondary mist by the mist refining device 240 to the inside of an isolator (not shown) (see FIG. 4 A).

Subsequently, the action of the hydrogen peroxide solution mist 232 and the fine mist 233 inside the mist supply device 210 according to the above configuration will be described with reference to FIGS. 4A, 4B.

Ultrasonic vibration of the ultrasonic speaker 63 of each of the vibration boards 241 in this state (see FIG. 2) generates significantly directional sound flows traveling in the vertical direction from the vibration surface 241a (indicated by arrows from board surfaces in FIG. 4B). The sound flow generated from the vibration surface 241a of the vibration board 241 acts on the hydrogen peroxide solution mist 232 discharged from the nebulizer 231 together with the sound flow reflecting off the reflection board 242. The hydrogen peroxide solution mist 232 travels upward in the figure shown (in the direction of the supply port 250) by a releasing pressure from the nebulizer 231. At this time, the hydrogen peroxide solution mist 232 is highly refined into the fine mist 233 by ultrasonic vibration by the sound flows generated from the vibration surface 241a and the sound flows reflecting off the reflection board 242, and diffuses upward and in the right/left direction shown in FIG. 4A to be supplied from the supply port 250 to the inside of an isolator (not shown).

The fine mist 233 diffused upward or in the right/left direction from the supply port 250 is pressed by the acoustic radiation pressure by a sound flow generated from a portion of the vibration surface 241a of the vibration board 241 that is not opposite the reflection board 242 to be circulated and dispersed inside the isolator. This state is indicated by open arrows in FIG. 4A and FIG. 4B.

In fact, since the fine mist 233 is refined by ultrasonic vibration to have smaller particle sizes and larger surface areas, it is believed that the evaporation efficiency of mists is high, resulting in repeated evaporation and condensation. The fine mist 233 is a highly-refined mist to form a uniform and thin condensed film on an internal wall surface of the isolator and external surfaces of onboard equipment disposed therein. Therefore, no excessive condensation occurs on internal wall surfaces of the isolator or external surfaces of internal equipment.

Accordingly, the fine mist 233 of hydrogen peroxide is subjected to ultrasonic vibration to be supplied to the inside of the isolator, thereby allowing the resulting repeated evaporation, condensation and refinement to provide decontamination effects. Accordingly, inside the isolator, ultrafine particles of hydrogen peroxide 3 μm or less and a hydrogen peroxide gas are subjected to phase change for coexistence to provide high-level decontamination environment.

Also, by repeated re-evaporation and condensation of the uniformly and thinly formed condensed film on the internal wall surfaces of the isolator and the external surfaces of internal equipment, the concentration of a decontamination agent in a fine mist 233 can be increased and efficient decontamination can be performed with a small amount of decontamination agent. Such an efficient decontamination with a small amount of decontamination agent can improve the efficiency of aeration for a condensed film of the fine mist 233 that is residual inside an isolator and reduce the duration of decontamination operations.

As stated above, according to each of the above embodiments, the present invention can provide a mist supply device capable of accomplishing a decontamination effect with a proper amount of decontamination agent supplied to a room to be decontaminated by converting a decontamination agent into a fine mist, and reducing the duration of operations such as aeration to achieve more efficient decontamination works.

Example

Figure 5:
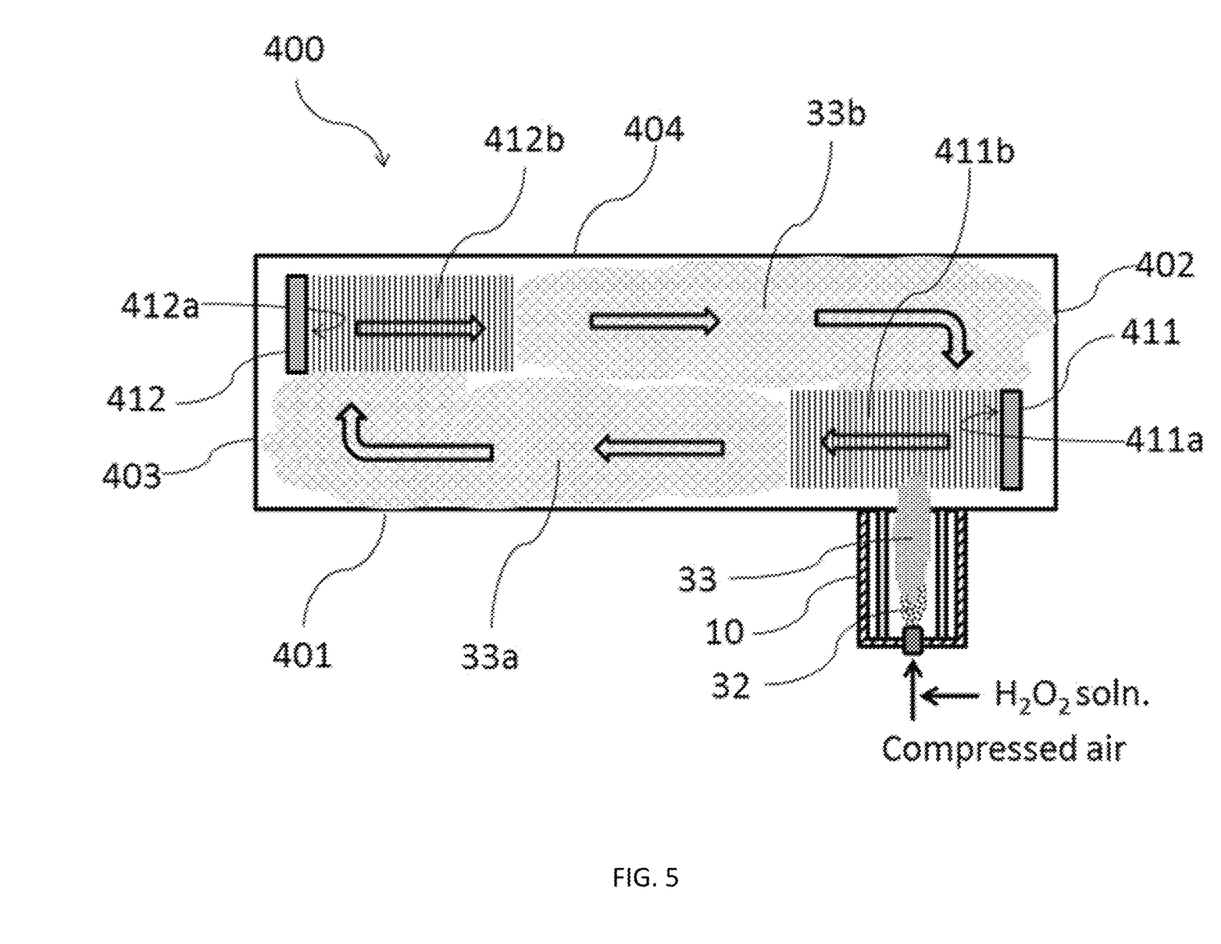
FIG. 5 is a schematic cross-sectional view showing the inside of an isolator including the mist supply device according to the first embodiment from the side.

Herein, the state of the mist supply device according to the above configuration in use will be described with reference to the example. FIG. 5 is a schematic cross-sectional view showing the inside of an isolator including the mist supply device according to the first embodiment from the side.

In FIG. 5, an isolator 400 includes a mist supply device 10 according to the above first embodiment outside a bottom wall surface 401 thereof. The mist supply device 10 is configured as described above. In this example, the decontamination agent used is a hydrogen peroxide solution (35 W/V %).

In this example, 2 ultrasonic vibration plates 411, 412 were employed for circulation and dispersion of a fine mist 33 supplied to the inside of the isolator 400 from the mist supply device 10. The circulation and dispersion of the fine mist 33 is not restricted to an ultrasonic vibration plate, and an ordinary circulating fan may be employed.

Herein, the circulation and dispersion of the fine mist 33 inside the isolator 400 will be described. In this example, the isolator 400 includes therein 2 vibration boards 411, 412. The 2 vibration boards 411, 412 are disposed inside the isolator 400 against side wall surfaces 402, 403 at 2 portions: a right wall surface lower portion and a left wall surface upper portion shown such that vibration surfaces 411a, 412a face horizontally inside the isolator 400. These 2 vibration boards 411, 412 are arranged without allowing board surfaces (vibration surfaces) to be opposite each other (the board surfaces to face each other in front). The reason for arranging the 2 vibration boards 411, 412 without being opposite each other and the action of a fine mist 33 will be described later. The structure of the vibration board 411 (also applied to the vibration board 412) is the same as that of a plurality of ultrasonic speakers arranged in a speaker base described in the above first embodiment (see FIG. 2).

Subsequently, the action of a fine mist 33 supplied to the inside of the isolator 400 from a mist supply device 10 will be described. In FIG. 5, the vibration board 411 disposed at the right lower portion shown inside the isolator 400 allows a vibration surface 411a thereof to face in the left direction shown. Ultrasonic vibration of the ultrasonic speaker 63 in this state (see FIG. 2) allows a significantly directional sound flow 411b traveling in the air in the vertical direction (in the left direction shown) from the vibration surface 411a to take in the fine mist 33 supplied from the mist supply device 10 to move the same in the direction of the sound flow 411b (in the left direction shown) by a pressing force from acoustic radiation pressure. The fine mist 33 is further refined into a fine mist 33a by ultrasonic vibration from the sound flow 411b to be circulated and dispersed inside the isolator 400.

Meanwhile, the vibration board 412 disposed at the left upper portion shown inside the isolator 400 allows a vibration surface 412a thereof to face in the right direction shown. Ultrasonic vibration of the ultrasonic speaker 63 in this state (see FIG. 2) allows a significantly directional sound flow 412b traveling in the air in the vertical direction (in the right direction shown) from the vibration surface 412a to press the fine mist 33a refined and sent by the sound flow 411b from acoustic radiation pressure to move the same in the direction of the sound flow 412b (in the right direction shown). The fine mist 33a is converted into a more stable fine mist 33b by ultrasonic vibration from the sound flow 412b to be circulated and dispersed inside the isolator 400.

Thus, the vibration boards 411 and 412 are disposed such that the respective vibration surfaces 411a, 412a are not opposite each other in front inside the isolator 400. In cases where the vibration surface 411a of the vibration table 411 and the vibration surface 412a of the vibration table 412 are opposite each other in front, the vibration boards 411 and 412 generate ultrasounds and their interaction generates a stationary sound wave field. This is attributed to the inability of the fine mists 33a, 33b to move due to no pressing force by acoustic radiation pressure.

Thus, fine mists 33a, 33b refined and stabilized by the sound flows 411b and 412b circulate so as to rotate in the arrow direction shown (clockwise) inside the isolator 400. The sound flows 411b and 412b, which are a stable stationary longitudinal wave traveling on a plane or planar surface, are transmitted as airflow having no difference in wind velocity compared to a direct type from a mist nozzle or a fan type.

In fact, since the fine mists 33a, 33b are further refined by ultrasonic vibration to have smaller particle sizes and larger surface areas, it is believed that the evaporation efficiency of mists is high, resulting in repeated evaporation and condensation. The fine mists 33a, 33b are highly-refined mists to form a uniform and thin condensed film on an internal wall surface of the isolator 400. Therefore, as opposed to conventional decontamination operations, no partial, uneven or thick condensed film is formed on the internal wall surface of the isolator 400.

Thus, the fine mists 33a, 33b of hydrogen peroxide are subjected to constant ultrasonic vibration to be circulated with repeated evaporation, condensation, and refinement inside the isolator 400. Even on the internal wall surface of the isolator 400, the fine mists 33a, 33b are subjected to constant ultrasonic vibration to cause repeated re-evaporation and condensation of a uniform and thin condensed film. Accordingly, it is believed that ultrafine particles of hydrogen peroxide 3 μm or less and a hydrogen peroxide gas are subjected to phase change for coexistence inside the isolator 400 to provide a high-level decontamination environment.

Also, by repeated re-evaporation and condensation of the uniformly and thinly formed condensed film on the internal wall surface of the isolator 400, the concentration of a decontamination agent in a decontamination mist can be increased and efficient decontamination can be performed with a small amount of decontamination agent. Such an efficient decontamination with a small amount of decontamination agent can improve the efficiency of aeration after decontamination and reduce the duration of decontamination operations. Furthermore, the secondary effect is that ultrasonic vibration and acoustic radiation pressure by the sound flows 411b and 412b can remove a deposit on the internal wall surface of the isolator 400.

Accordingly, in this example, the fine mist 33 supplied to the inside of the isolator 400 is already highly refined, and it is subjected to constant ultrasonic vibration from acoustic waves of 2 vibration boards 411, 412 inside the isolator 400 to repeat evaporation, condensation and refinement inside the isolator 10. A pressing force by acoustic radiation pressure from acoustic waves circulates the inside of the isolator 400. Thus, in this example, the mist supply device according to the present invention can effectively be utilized to achieve efficient decontamination.

The goals of the present invention are achieved by not only each of the above embodiments, but also by the following various alternatives.

(1) In the above embodiments, vibration boards of a mist supply device used include a plurality of ultrasonic speakers arranged in a speaker base. However, the vibration boards are not restricted thereto, and any type of vibration board may be used so long as it includes a Langevin type transducer fixed to a stainless steel having a constant area or a board surface for ultrasonic vibration.

(2) In the above embodiments, vibration boards of a mist supply device used include a plurality of ultrasonic speakers arranged in a speaker base so as to be uniform in transmission directions of the transmitters, and the transmitters are operated in the same phase. However, the vibration boards are not restricted thereto, and a plurality of ultrasonic speakers may be operated in a different phase.

(3) In the above embodiments, the decontamination agent used is a hydrogen peroxide solution ($H_2O_2$ solution). However, the decontamination agent is not restricted thereto, and it may be any type of decontamination agent so long as it is liquid.

REFERENCE SIGNS LIST 10, 110, 210 . . . Mist supply device, 20, 120, 230 . . . Housing,
21, 22, 23, 24, 121, 122, 123, 124, 221, 222 . . . Wall surface,
30, 130, 230 . . . Mist generator,
31 . . . Two-fluid spray nozzle, 131, 231 . . . Nebulizer,
31a, 131a . . . Mist discharge port, 131b . . . Main container,
131c, 231c . . . Ultrasonic vibrator,
32, 132, 232 . . . Hydrogen peroxide solution mist, 33, 133,
233 . . . Fine mist,
40, 140, 240 . . . Mist refining device,
41, 42, 141, 142, 241 . . . Vibration board, 242 . . . Reflection board,
41a, 42a, 141a, 142a, 241a . . . Vibration surface,
242a . . . Reflection surface,
50, 150, 250 . . . Supply port,
61 . . . Speaker base, 62 . . . Plane or planar surface of speaker base,
63 . . . Ultrasonic speaker, 64 . . . Vibration surface of ultrasonic speaker,
400 . . . Isolator, 301, 302, 401, 402, 403, 404 . . . Wall surface,
411, 412 . . . Vibration board, 411a, 412a . . . Vibration surface,
411b, 412b . . . Sound flow.

The invention claimed is:

1. A mist supply device configured to convert a decontamination agent into a mist and to supply the mist to an inside of a room to be decontaminated, the device comprising:
a mist generation means, a mist microparticulating means, and a supply port, wherein:
the mist generation means is configured to convert the decontamination agent into a primary mist and to supply the primary mist to the mist microparticulating means,
the mist microparticulating means includes one or more vibration boards, and is configured
to generate sound flows directed from surfaces of said one or more vibration boards in directions perpendicular to said surfaces when subjected to ultrasonic vibration caused by an ultrasound,
to further refine the primary mist, supplied from the mist generation means, to a secondary mist by exposing the primary mist to ultrasonic vibration caused by the sound flows,
and
the supply port is configured to receive said secondary mist from the mist microparticulating means and to transfer said secondary mist therethrough to the inside of the room to be decontaminated due to a releasing pressure of the primary mist from the mist generation means.

2. The mist supply device according to claim 1, wherein:
the mist generation means includes a single-fluid spray nozzle or a two-fluid spray nozzle, or an ultrasonic mist generator that contains an ultrasonic humidifier or a nebulizer.

3. The mist supply device according to claim 2, wherein:
the one or more vibration boards of the mist microparticulating means include one or more pairs of vibration boards,
the one or more pairs of vibration boards are arranged with board surfaces thereof being opposite each other from an outer peripheral side of a flow of the primary mist supplied from the mist generation means to control the ultrasonic vibration caused by the sound flows to concentrate on the primary mist.

4. The mist supply device according to claim 3, wherein:
a vibration board from the one or more vibration boards includes a base and a plurality of transmitters,
the plurality of transmitters is arranged on a planar surface of the base spatially-uniformly, and transmitters from said plurality are configured to be operated in the same phase to mutually amplify ultrasound outputs produced by said transmitters in a front direction and mutually cancel ultrasound outputs produced by said transmitters in a lateral direction, thereby generating
a sound flow with a significantly directional ultrasound emanating from a board surface of said vibration board in the vertical direction.

5. The mist supply device according to claim 2, wherein:
the mist microparticulating means comprises a combination of one or more pairs of a vibration board and a reflection board, said combination being arranged with respectively corresponding vibration board surfaces and reflection board surfaces being opposite to an outer peripheral side of a flow of the primary mist supplied from the mist generation means to control the ultrasonic vibrations caused by the sound flows generated at the vibration boards and by sound flows reflecting off of the reflection boards and to concentrate said ultrasonic vibrations on the primary mist.

6. The mist supply device according to claim 5, wherein:

the supply port includes at least some board surfaces of the vibration boards as a supply means of the secondary mist, and the device is configured to press the secondary mist with acoustic radiation pressure caused by sound flows generated from said at least some board surfaces to supply the secondary mist to the inside of the room to be decontaminated.

7. The mist supply device according to claim 6, wherein:

a vibration board from the one or more vibration boards includes a base and a plurality of transmitters, the plurality of transmitters is arranged on a planar surface of the base spatially-uniformly, and transmitters from said plurality are configured to be operated in the same phase to mutually amplify ultrasound outputs produced by said transmitters in a front direction and mutually cancel ultrasound outputs produced by said transmitters in a lateral direction, thereby generating a sound flow with a significantly directional ultrasound emanating from a board surface of said vibration board in the vertical direction.

\* \* \* \* \*